(12) United States Patent
Elkins

(10) Patent No.: US 6,178,562 B1
(45) Date of Patent: Jan. 30, 2001

(54) CAP AND VEST GARMENT COMPONENTS OF AN ANIMATE BODY HEAT EXCHANGER

(75) Inventor: William Elkins, Sant Clara County, CA (US)

(73) Assignee: Coolsystems, Inc, Berkeley, CA (US)

( * ) Notice: Under 35 U.S.C. 154(b), the term of this patent shall be extended for 0 days.

(21) Appl. No.: 09/493,746

(22) Filed: Jan. 28, 2000

(51) Int. Cl.⁷ .............................. A61F 7/00; A41D 1/04; A42B 1/04

(52) U.S. Cl. .................. 2/458; 2/81; 2/102; 2/171.2; 62/259.3; 607/108; 607/110

(58) Field of Search .................. 2/69, 102, 81, 2/93, 94, 108, 458, 171.2, 181, 174, 209.13, 171.3, 413, 414, 456; 62/259.3, 530; 165/46; 607/104, 108, 109, 110, 114

(56) References Cited

U.S. PATENT DOCUMENTS

| | | | |
|---|---|---|---|
| 3,261,042 | * | 7/1966 | Baker ........................................ 2/102 |
| 3,320,682 | * | 5/1967 | Sliman ................................. 607/110 |
| 3,738,367 | * | 6/1973 | Hardy ................................... 62/259.3 |
| 4,147,921 | * | 4/1979 | Walter et al. ........................ 607/110 |
| 4,738,119 | * | 4/1988 | Zafred ................................... 62/259.3 |
| 5,002,270 | * | 3/1991 | Shine ....................................... 2/102 |
| 5,163,425 | * | 11/1992 | Nambu et al. ....................... 607/110 |
| 5,353,605 | * | 10/1994 | Naaman ............................. 62/259.3 |
| 5,564,124 | * | 10/1996 | Elsherif et al. ........................... 2/69 |
| 5,792,216 | * | 8/1998 | Kappel ................................. 607/107 |
| 5,913,885 | * | 6/1999 | Klatz et al. .......................... 607/104 |
| 5,967,225 | * | 10/1999 | Jenkins .................................. 165/46 |
| 5,970,519 | * | 10/1999 | Weber ...................................... 2/81 |

* cited by examiner

Primary Examiner—Amy B. Vanatta
(74) Attorney, Agent, or Firm—C. Michael Zimmerman

(57) ABSTRACT

Cap and vest components of an animate body heat exchanger designed to apply a controlled temperature to parts of a human body are described. The cap and vest components are often used in combination, and the interior side edges of the cap are curvilinear and intermesh lengthwise to assure that the portion of the head underlying the junction between such edges is subjected to the controlled temperature. The vest includes not only a zipper for application and removal, but also separate lacing for close fitting adjustment.

22 Claims, 5 Drawing Sheets

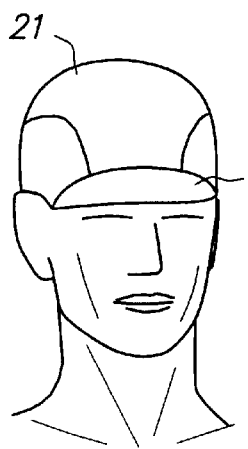 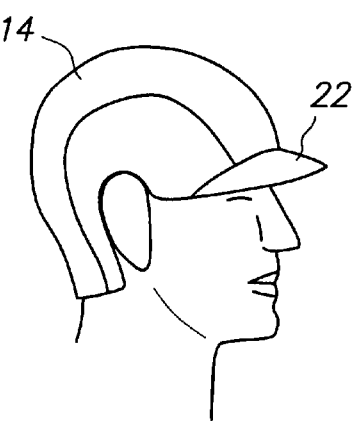 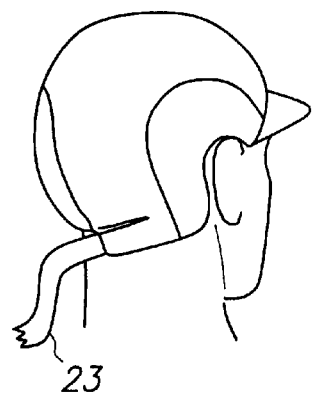
FIG. 3A  FIG. 3B  FIG. 3C
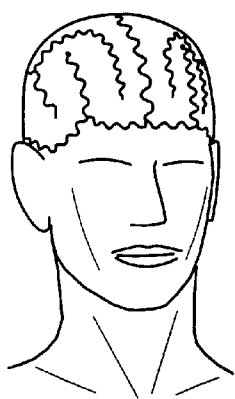 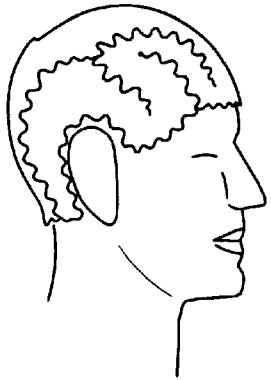 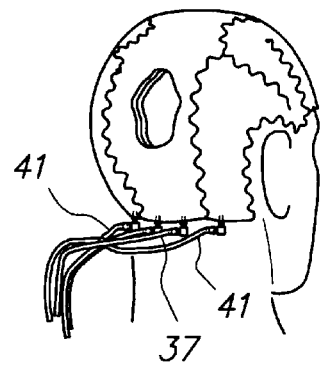
FIG. 4A  FIG. 4B  FIG. 4C
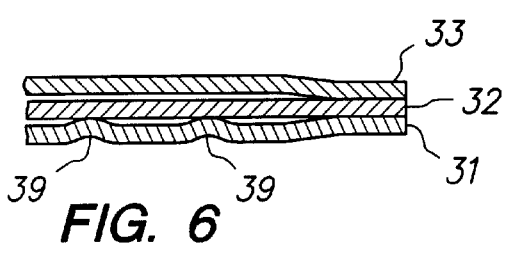 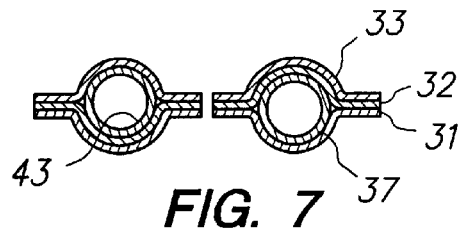
FIG. 6  FIG. 7

CAP AND VEST GARMENT COMPONENTS OF AN ANIMATE BODY HEAT EXCHANGER

BACKGROUND OF THE INVENTION

This present invention relates to temperature control apparatus for parts of a human or other animate body and, more particularly, to thermal contact components of an animate body heat exchanger that assure quite good thermal contact with associated body parts.

Active cooling arrangements for humans and other animate bodies (live bodies, except for the live bodies of plants) are known. They either are used, or contemplated for use, in physical therapy, pre-game conditioning, minor injury care, etc. In general, the body heat exchanging component(s) of such an apparatus has a pair of layers defining a flexible bladder through which a liquid is circulated. This liquid is maintained at a desired temperature. Generally, the desired temperature is lower than the temperature expected for the body part, and typically is achieved, at least in part, by passing the liquid through a "passive" heat exchanging medium, such as by passing the same through an ice bath.

It is quite important in many arrangements of this nature that the amount of heat exchange be carefully controlled. This means that the temperature to which the body part is subjected must be kept constant. Moreover, for some uses it is important that all of the surface area covered by a heat exchange component be subjected to the temperature control.

Various improvements have been made in the past in an effort to obtain the desired known temperature control. For example, units are made which are quite thin and flexible to facilitate conforming to the complex shape of a body part to be subjected to temperature control. Pressurized air bladders are also used to press a flexible fluid bladder into intimate contact with an associated body part. Matrices of point (dot) connections and fences (flow directing devices) are also included in many fluid bladders to provide the fluid mixing and flow pattern needed to obtain the desired constant flow of liquid having a constant temperature through a heat exchange component.

The above measures have been taken to assure that a heat exchange component design remains quite thin and does not buckle when it conforms to complex shapes, so as to remain in good thermal contact with a body part. Moreover, the shape of the fences and bladder edge contours are selected to inhibit the formation of eddies, again in an effort to assure proper flow for a constant and controlled temperature differential with a body part.

BRIEF DESCRIPTION OF THE INVENTION

This invention relates to two innovations which are quite important in designing heat exchange components for body parts that provide known, repeatable and uniform thermal conductance with such body parts.

In basic terms, one of the such innovations is providing a configuration for adjacent side edges of a bladder shaped to generally conform to a body part, such as a head, so that such edges will intermesh lengthwise with one another. This intermeshing is facilitated by furnishing the border of each of the adjacent edges with curvilinear ripples, each of which has a length considerably shorter than the total length of the side edge to be intermeshed.

The side edge intermeshing facilitates providing a structure which assures that the portion of the body part underlying the junction between the two sides is subjected to the temperature differential provided by the temperature control fluid within the bladder. In this connection, as mentioned earlier one of the major criteria for some uses of the invention is to assure that all covered surface areas of the body part is subjected to the control temperature provided by the component.

The intermeshing configuration is preferably selected to eliminate any straight line flow of the fluid, typically a liquid, along such junction. This aids in assuring that the intermeshing function is not circumvented by temperature controlled fluid "bypassing" the intermeshing. Moreover, such configuration is preferably selected to prevent eddy flow. The curvilinear ripple of the preferred embodiment of the invention provide such a configuration.

The other innovation of the invention incorporated into a heat exchange component has to do with assuring that the amount of contact pressure between a body part and the heat exchange component and, hence, the amount of energy transferred therebetween, is repeatable from one use to another. This innovation includes providing an adjustment mechanism in the component for setting the distance between sides which are contiguous (near, but not touching) with one another lengthwise as well as including in the component, a separate opening and closing mechanism for use in applying the component to the body part. The provision in one component of both of these mechanisms assures that the setting used at one time can also be used at a later time, i.e., the amount of pressure provided by the garment is repeatable since it is a separate mechanism used for applying the component to the body part.

Most simply, lacing along the contiguous sides provides the desired relatively permanent adjustment. The separate opening and closing mechanism, can be a zipper or buttons, such as at the front in a vest garment. In this connection, a vest is a type of component for which this innovation is particularly applicable.

A combination of the innovations of this invention with other aspects of a heat exchanger component results in an overall arrangement which has significantly improved performance. Other features and advantages of the invention either will become apparent or will be described in connection with the following, more detailed description of preferred embodiments of the invention and variations.

BRIEF DESCRIPTION OF THE DRAWINGS

With reference to the accompanying drawings:

FIGS. 3A, 3B, and 3C are differing views of a preferred embodiment of a heat exchange component of the invention configured for a human head, a body part having a complex shape;

FIGS. 4A, 4B, and 4C are views similar to the views of FIG. 3, showing the interior configuration of the component;

FIG. 6 is a partial sectional view, generally indicated by the plane represented by the lines 6 in FIG. 5;

FIG. 7 is another partial sectional view taken on a plane indicated by the lines 7 in FIG. 5;

DETAILED DESCRIPTION OF THE PREFERRED EMBODIMENTS

The following, relatively detailed description is provided to satisfy the patent statutes. It will be appreciated by those skilled in the art, though, that various changes and modifications can be made without departing from the invention.

Figure 1:
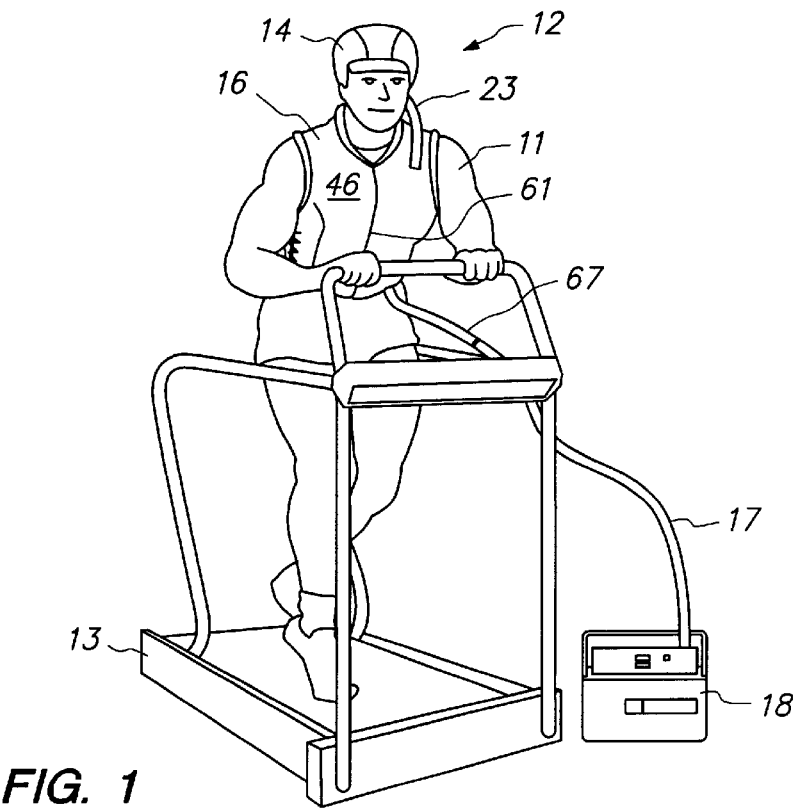
FIG. 1 is an overall isometric illustration showing a preferred embodiment of the invention being utilized by a human during exercise.

A male human subject is shown at 11 in FIG. 1 wearing a preferred embodiment 12 of the invention and working out on a treadmill 13. Such preferred embodiment includes both a cap garment 14 and a vest garment 16 connected via a cord 17 to a temperature control device 18. The cord 17 contains the fluid conduits as will be described in more detail hereinafter. As also will become clear from the following, the temperature control fluid most desirably is a liquid because of many things, including the relatively high thermal capacity of a liquid relative to the thermal capacity of a gas. The conduit in associated bladder for the pressure fluid typically is an air or other gas conduit.

The preferred embodiment of the invention being described is designed to apply a controlled, low temperature to parts of a human body. In this connection, the device 18 includes not only a circulator for circulating a desired low temperature liquid, but also a heat exchange unit for removing heat from the same. It further includes means for maintaining a precise liquid temperature, as well as means for supplying pressurized air.

Although the pressure of the air and the controlled temperature for the circulating liquid are selected in accordance with known principles for particular uses, the liquid pressure typically is between 10 and 15 psig and its temperature is between 45°–50° F. The liquid could be, for example, a 20 percent propylene glycol solution in distilled water with a small amount of a wetting agent to break surface tension, and an anti-fungicide such as iodine. The pressure of air also depends on a particular use, but is generally between about 0.25 and 1.5 psig. (In many instances it is cycled between these extremes.) The nominal pressure selected in one implementation of the cap-vest combination of the invention was 0.25 psig.

An important aspect of the invention relates to the cap 14 of the cap-vest combination of the invention. References is made to FIGS. 3 through 7 for a detailed description of the same. It includes a covering 21 (FIGS. 3A–3C) having a bill 22. The covering 21, besides providing the typical visual arrangement normally associated with a cap, hides the underlying, operational layers of the invention. The covering most desirably includes an insulating layer, such as a layer of "Thinsulate," to thermally isolate the operational layers of the invention from the ambiant environment. (The cap illustrated in FIGS. 3–7 is designed for a male. As illustrated in FIG. 2B, a female cap may be slightly different, e.g., have a smaller bill.) A cord covering 23 is shown in FIG. 3C for the fluid inlet and outlet tubes for such operational layers.

As mentioned previously, one of the major challenges in designing a heat exchange component for many body parts having a complex shape is to assure there is a close fit between the heat exchange component and the body part. That is, the heat exchange component preferably not only has a configuration which generally is complementary to the shape of the body part, it is also quite compliant so that it can conform to individual variations in the body part shape. This conformance helps immeasurably in assuring good thermal contact between the body part and the heat exchange component.

As also mentioned previously, the head of a human is quite a complex shape, with individual heads varying in size and in shape details. It is quite important, though, when one provides heat exchange with a human head that all aspects of the same be subjected to the same controlled temperature, i.e., that the heat exchange component provide a uniform flow of a coolant liquid over all areas of the head.

Figure 5:
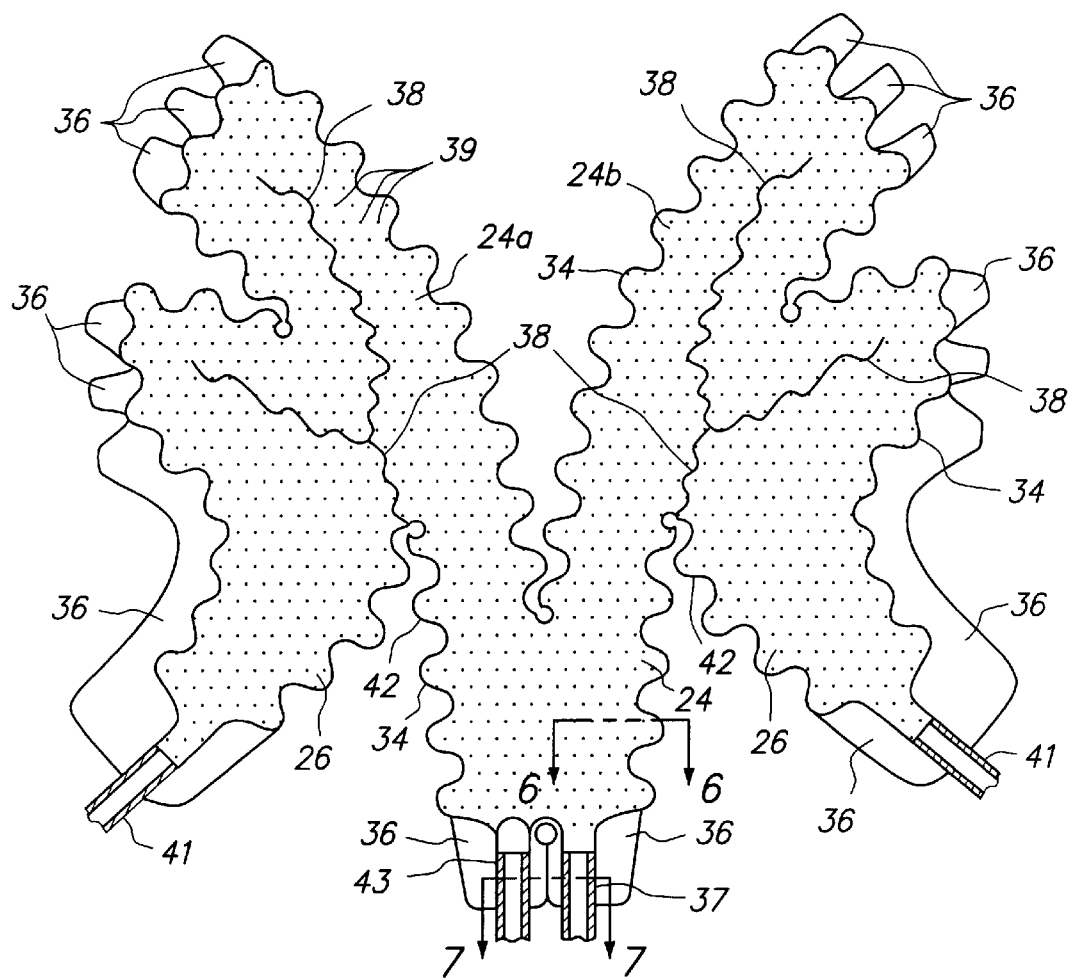
FIG. 5 is an elevation view of a layer for a liquid bladder of the component of FIGS. 3 and 4, showing the bladder configuration and how adjacent sides of the layers intermesh.

It will be recognized for a heat exchange component to be configured in the three-dimensional complex shape of a human head, it must form a relatively intricate pattern when it is two dimensional. FIG. 5 illustrates such an intricate pattern. In this connection, FIG. 5 shows a fluid flow layer of the liquid bladder of the aspect of the invention being described. It includes a central rear lobe 24 and a pair of opposed side lobes 26. The central lobe 24 is divided into two sublobes 24a and 24b which diverge from one another as illustrated. The manner in which such lobes form a complex shape generally conforming to a human head may be seen by comparing FIG. 5 with FIGS. 4A–4C.

The heat exchange component of the invention is made up of three layers of quite flexible, compliant materials. These three layers define a pair of compliant fluid bladders, a liquid bladder defining a chamber for the flow of a temperature controlled liquid, and an air pressure bladder shaped and positioned to apply pressure individually against the first bladder to press the latter into intimate contact with the head. FIG. 6 is a cross-sectional view of such three layers. (Section lines are omitted for clarity.)

The gas pressure bladder, the second bladder, is defined by a third outer layer 33 and the free side of layer 32. In this connection, such layer 32 also is selected to be impermeable to the gas used for pressurization.

This outer layer 33 desirability is elastic in order to minimize buckling of the liquid bladder when the air bladder is expanded by pressurized air. Suitable fabric for such layer is a stretchable nylon or coated polyester knit.

As illustrated, the three layers have a common border which defines the side edge which provides the intermeshing. This common border is labeled with a reference number 34 in FIG. 5 and is shaped with the curvilinear ripples. One of the layers extends beyond the border 34 to define connection tabs 36 for use in securing the bladders to the interior of the covering (as mentioned previously, the covering most desirably also includes a ply of an insulating material to isolate the bladders from their environment—it should be noted that to simplify the drawings the connecting tabs 36 are not shown in FIGS. 4A–4C.)

Temperature control liquid is introduced to the liquid bladder via a tube 37. It flows through the bladder along paths defined by the border 34 and "fences" (interior dividers) 38. The layers 31 and 32 defining the liquid bladder are adhered together at a multitude of regularly spaced points or dots 39 to define a matrix of connections which will assure good mixing and uniform flow of the temperature controlled liquid as it passes through the liquid bladder to exits defined by tubes 41 at the ends of the respective lobes 26.

It is the common side edge border 34 of the bladders which provides the intermeshing. As best illustrated in FIG. 5, each of such borders is provided along its length with a plurality of curvilinear ripples 42. The curvilinear ripples on adjacent side edges are complementary with one another and each is significantly shorter lengthwise than the side edge of which it is a part. It will be seen that these ripples not only provide the desired intermeshing, but also eliminate any straight line path for flow of cooling liquid along the junctions defined by the intermeshing. Moreover, the ripple configuration inhibits the formation of eddies along the junctions between adjacent sides. In this connection, it is to be noted that the matrix of the connections 39 extends into the ripples.

As brought out earlier, the showing in FIG. 5 is only of one of the layers, the layer 31, making up the liquid bladder. The tube for delivering pressure to the air bladder, tube 43, is included and is part of the showing. FIG. 7 shows the manner in which the adjacent liquid and gas tubes communicate with their respective bladders even though they are provided adjacent one another. It will be noted that the layer 33 has a common border with the layer 31 and 32 but that there is not a matrices of connection points between the layers 32 and 33, i.e., in the gas bladder. This gas bladder, when pressurized, presses the layer 31 against the body part for good thermal contact. In this construction it does so indirectly through the layer 32 by pressing the full liquid bladder against the body part.

Figure 8:
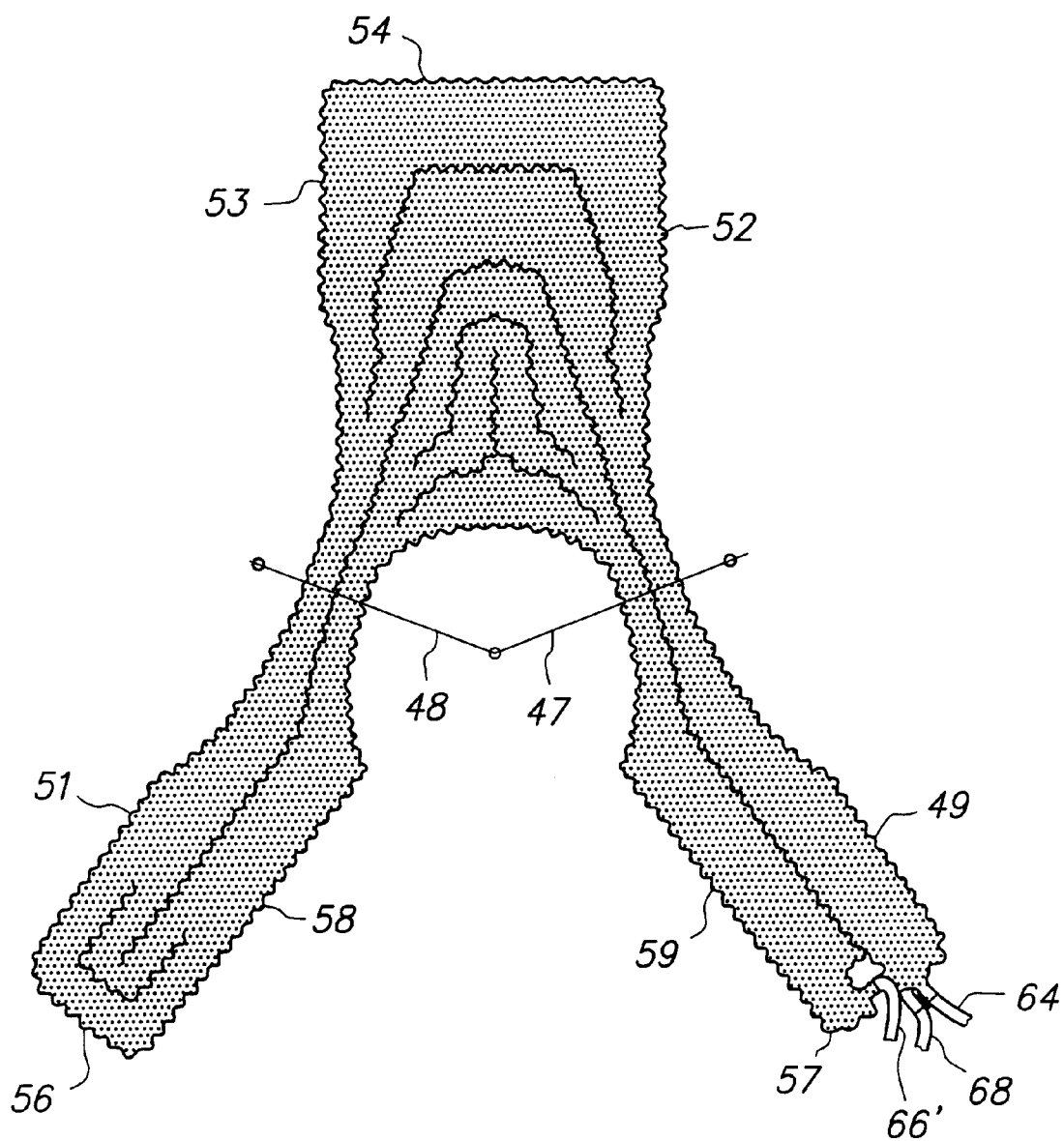
FIG. 8 is an elevation view of a layout of the liquid bladder of a vest garment incorporating a preferred embodiment of the second innovation of the invention.

The tube cord 23 directs the various tubes into vest garment 16. This vest garment includes not only a covering 46 but also three layers defining gas and liquid bladders as is typical. FIG. 8 illustrates the outlying and connection pattern for one of the liquid bladder layers. This layer is defined by a coated flexible material as described earlier and is folded over with the rest of the vest garment, generally at locations represented by the lines 47 and 48. The result is that the side edges 49 and 51, respectively, are positioned contiguously, respectively, to side edges 52 and 53. The border represented at 54 is then located at the small of the back of the wearer, whereas the borders 56 and 57 are then located at the front waist of the wearer. The borders 58 and 59 are adjacent one another at the center-front of the torso of a wearer as will be described.

Figure 2A:
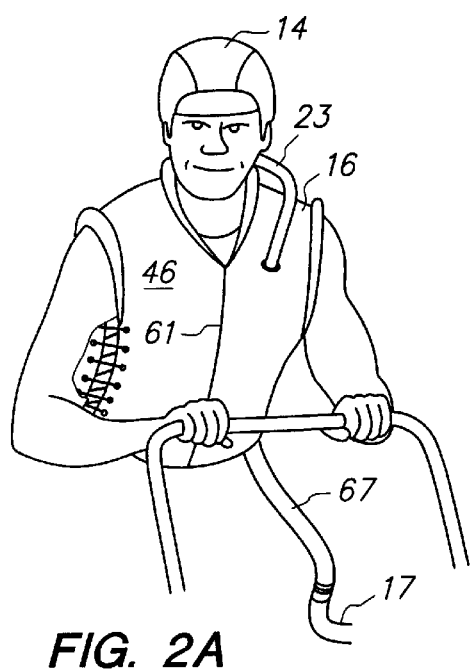
FIGS. 2A and 2B are enlarged views of the preferred embodiments of the invention as configured respectively for male and female humans.
Figure 2B:
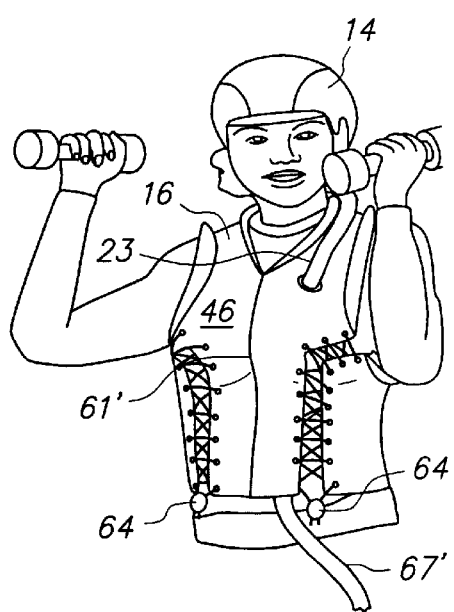

The edges of the garment along the sides are contiguous to one another and are laced together as is illustrated in FIGS. 1 and 2A. (It is to be noted that it is a covering that is laced together.

The layout described above is for a male vest and the covering lacing is illustrated in FIGS. 1 and 2A. In this connection, the arm of the wearer is broken away in FIG. 2A to show such construction on one side—it will be recognized that the same lacing construction is provided on the opposite side of the garment.

As a salient feature of the instant invention, the garment construction also includes a separate opening and closing mechanism along the center-front of the garment. In this preferred embodiment, a zipper represented at 61 provides this separate opening and closing mechanism. It should be noted that it is not necessary that it be a zipper. For example, a button and buttonhole arrangement also could be utilized. What is important is that the opening and closing mechanism be separate from the adjustment mechanism provided by the side lacing. This enables the garment to be applied or taken off from the torso without any interference with the tension adjustment provided by the lacing. Thus, the incorporation of this innovation in a heat exchange component enables one to obtain a repeatable thermal contact with a body part.

Figure 9:
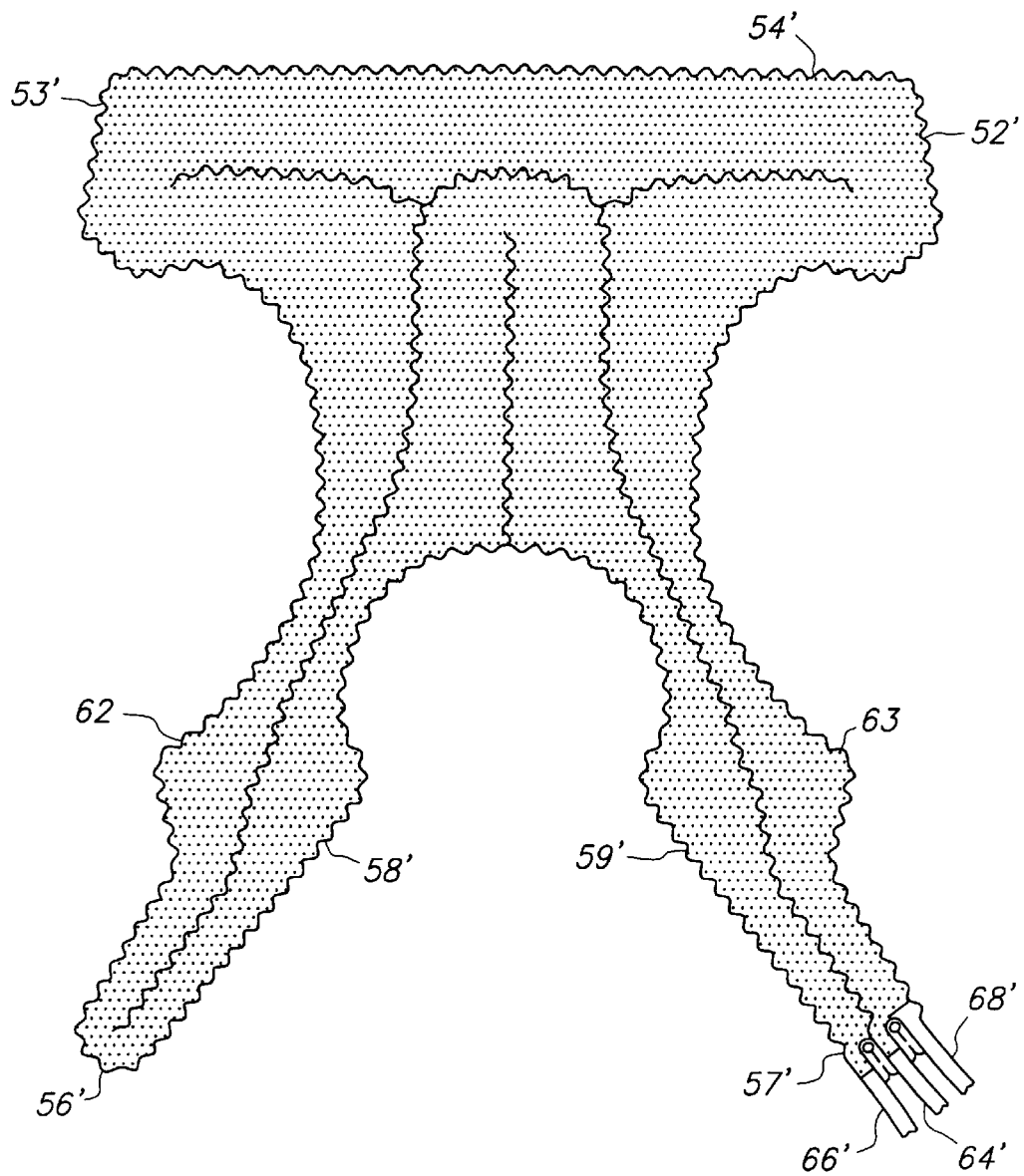
FIG. 9 is a view similar to that of FIG. 8 of a liquid bladder layout for a female vest garment of a preferred embodiment of the invention.

The layout illustrated in FIG. 8 is for a vest garment of the invention designed for the torso of a human male. FIG. 9 shows a comparable layout for a female. The male and female layouts are quite similar in concept, and like parts of the layout for the female vest garment are referred to by the same numerals used with the male layout, primed. It is different in that the layout takes into account the fact that the lacing also enables adjustment to accommodate different breast sizes as is shown in FIG. 2B. Thus the side edges comparable to the side edges 49 and 51 of the male layout include darts 62 and 63. In some uses, it may be desirable to have two separate lacing constructions at each of the contiguous sides, one for breast size adjustment and the other for thermal contact adjustment along the remainder of the sides. In this preferred embodiment, the lacings pass through conventional grasps represented at 64. It will be appreciated that grasps of this nature are also provided for the lacings of the male vest.

Liquid is first circulated through the cap garment and then circulatd through the vest garment. That is, the liquid which exits the head garment through tubes 41 is introduced into the associated vest garment through tubes 64 and 64'. It then exits the vest through the tubes 66 and 66' and passes through a cord 67 coupled to cord 17 and, hence, temperature control device 18. These cores also include, of course, the air pressure tubes 37 and 68.

The layers 31 and 32 define the first bladder. In this connection, the layers making up this liquid bladder are made generally impermeable to the liquid that is used. In the implementation in which the temperature controlled liquid was a propylene glycol solution as discussed earlier, each of such layers was a fabric laminated with coatings of an ether-based polyurethane, a thermoplastic which provided both the desired impermeability and enables heat welding. The fabric material of both of the layers 31 and 32 was a nylon having a two-hundred denier rating. Such fabric was coated with a relatively high density polyurethan ply sandwiched between a pair of relatively low density polyurethane plies.

As mentioned at the beginning of the detailed description, applicant is not limited to the specific embodiments and variations described above. For example, depending upon the design and use of components incorporating the invention, only one layer of the temperature controlled liquid bladder, the lower layer 31 may be flexible and pressed against the body part by the pressure bladder. The cap and vest innovations may be used separately, although best results are achieved in the implementation described when they are used together. Moreover, the circulating heat control fluid might be a gas instead of a liquid and the pressure fluid could be a liquid rather than a gas. The claims, their equivalents and their equivalent language define the scope of protection.

What is claimed is:

1. A component of an animate body heat exchanger, which component is designed for contact with a part of an animate body for heat exchange therewith, comprising: a pair of overlapping fluid bladders, a first one of which is designed to direct flow of a heat exchange fluid as desired and includes at least one layer of a compliant material enabling such layer to conform to individual variations in the shape of the body part, and a second of which is shaped and positioned to direct gas pressure against said layer to press the same into intimate contact with said body part; said layer having at least a pair of side edges which are contiguous lengthwise with one another when said layer is in a configuration which generally is complementary to the shape of said body part; an adjustment mechanism for setting the distance between said side edges; and a separate opening and closing mechanism for use in applying said component to said body part.

2. The component of claim 1 wherein said adjusting mechanism for setting the distance between said sides is lacing.

3. The component of claim 1 wherein said separate opening and closing mechanism for use in applying said component to said body part is a zipper.

4. The component of claim 1 wherein said component is a garment designed to encase said part, which garment is folded upon itself to provide said pair of side edges which are contiguous lengthwise with one another.

5. The component of claim 4 in which said component is formed into a configuration of a vest.

6. The component of claim 4 wherein when said garment is folded upon itself it provides two of said pair of sides which are contiguous lengthwise with one another.

7. The component of claim 6 in which said garment when folded is formed into the configuration of a vest for a female, and each of said pair of side edges is designed to be positioned at a breast of a female and provide adjustment of the garment thereat to breast size.

8. The component of claim 1 wherein said first one of said bladders includes at least two overlapping layers of compliant materials enabling this bladder to conform to individual variations in the shape of a body part, which layers are secured together at a multiplicity of uniformly spaced points that form a matrix of securance points, such points being positioned relative to the expected direction of flow of liquid through the bladder to provide mixing.

9. The component of claim 8 wherein said second bladder is formed by a third layer which cooperates with one of said overlapping layers to define such second bladder, the borders of all of said layers being secured together to form a common border providing said pair of side edges which are contiguous lengthwise with one another.

10. A component of an animate body heat exchanger, which component is designed for contact with a part of an animate body for heat exchange therewith, comprising: a pair of overlapping fluid bladders, a first one of which is designed to direct flow of a heat exchange fluid as desired and includes at least one layer of a compliant material enabling such layer to conform to individual variations in the shape of the body part, and the other of which is shaped and positioned to direct gas pressure against said layer to press the same into intimate contact with said body part; said layer having at least a pair of adjacent side edges which mate with one another lengthwise when said layer is in a configuration which generally conforms to the shape of said body part, said side edges themselves being configured to intermesh with one another along their length when said configuration is made.

11. The component of claim 10 further including an additional component for heat exchange with a differing part of said animate body than said component, said additional component also including a pair of overlapping fluid bladders, a first one of which is designed to direct flow of heat exchange fluid as is desired and includes at least one layer of a compliant material enabling such layer to conform to individual variations in the shape of such a differing body part, and the other of which is shaped and positioned to direct gas pressure against said layer of said additional component to press the same into intimate contact with said differing body part; said layer of said additional component also having at least a pair of side edges which are contiguous lengthwise with one another once said layer is in a configuration which generally is complementary to the shape of said differing body part; an adjustment mechanism is provided for setting the distance between the side edges of said additional component; and a separate opening and closing mechanism is also included for applying said additional component to said body part.

12. The component of claim 11 wherein said component is a cap for a human and said additional component is a vest for said human, with the first bladders of said components being in fluid communication with one another for the flow of the same in heat exchange fluid through both.

13. The component of claim 10 wherein the configuration of each of said edges is selected not only to provide said intermeshing but also to eliminate straight line passage for the flow of fluid interiorally of said bladder along an intermeshed portion of said side edges.

14. The component of claim 10 wherein the configuration of each of said side edges is selected not only to provide said intermeshing but also to inhibit the formation of eddies along the intermeshed side edges.

15. The component of claim 14 wherein the configurations of said side edges providing said intermeshing is a plurality of curvilinear ripples.

16. The component of claim 15 wherein said configuration is that of a cap generally conforming to the shape of a head of a human.

17. The component of claim 15 wherein each of said ripples has a length which is considerably shorter than the total length of the side edge to be intermeshed.

18. A garment component of an animate body heat exchanger, which component is designed for contact with a part of an animate body for heat exchange therewith, comprising: a pair of overlapping fluid bladders, a first one of which is for containing and directing flow of a heat exchange fluid as desired and the second one of which overlies the first one and is for directing gas pressure against said first one to press the same into intimate contact with said body part; said first one being made up of two spaced layers of a compliant material and the second of which is made up of a third layer of compliant material which cooperates with one of the layers of said first bladder to define a gas pressure chamber overlying said first bladder for said pressing, said component being shaped into a configuration complementary to said body part and having a pair of side edges made up of the three layers, said side edges being adjacent to one another lengthwise, and intermesh with one another along their adjacency.

19. The garment component of claim 18 wherein the configuration of said side edges providing said intermeshing is a plurality of curvilinear ripples.

20. The garment component of claim 19 wherein said garment component is a cap for a human and the body part defining the configuration of the shape of said component is a human head.

21. A garment component of an animate body heat exchanger, which component is designed for contact with the torso of a human for heat exchange therewith, comprising a pair of overlapping fluid bladders, the first one of which is for containing and directing flow of a heat exchange fluid as desired and the second one of which overlies the first one and is for directing gas pressure against the first one to press the said first one into intimate contact with said body part; said first one being made up of two spaced layers of a compliant material and the second one being made up of a third layer of compliant material which cooperates with one of said layers of said first bladder to define a gas pressure chamber overlying said first bladder for said pressing, said component being shaped into a configuration complementary to a human torso and, in connection therewith, being folded over to provide a pair of side edges which are contiguous with one another lengthwise; lacing connecting said sides for setting the distance between said sides; and a separate opening and closing mechanism for use in applying said garment to said human torso.

22. The component of claim 21 of an animate body heat exchanger wherein said separate opening and closing mechanism is a zipper.

* * * * *